United States Patent
Kwon

(10) Patent No.: US 10,125,360 B2
(45) Date of Patent: Nov. 13, 2018

(54) METHOD FOR SECRETION OF EXTRACELLULAR VESICLES FROM CELLS AND TISSUES USING SHOCK WAVE

(71) Applicant: EWHA UNIVERSITY—INDUSTRY COLLABORATION FOUNDATION, Seoul (KR)

(72) Inventor: Kihwan Kwon, Seoul (KR)

(73) Assignee: EWHA UNIVERSITY-INDUSTRY COLLABORATION FOUNDATION, Seoul (KR)

( * ) Notice: Subject to any disclaimer, the term of this patent is extended or adjusted under 35 U.S.C. 154(b) by 0 days.

(21) Appl. No.: 15/411,628

(22) Filed: Jan. 20, 2017

(65) Prior Publication Data

US 2017/0204396 A1    Jul. 20, 2017

(30) Foreign Application Priority Data

Jan. 20, 2016    (KR) .................. 10-2016-0006974

(51) Int. Cl.
*C12N 13/00* (2006.01)
*C12N 15/113* (2010.01)

(52) U.S. Cl.
CPC .......... *C12N 13/00* (2013.01); *C12N 15/1136* (2013.01); *C12N 2310/14* (2013.01); *C12N 2320/32* (2013.01)

(58) Field of Classification Search
None
See application file for complete search history.

(56) References Cited

FOREIGN PATENT DOCUMENTS

KR    10-2014-0054622    5/2014

OTHER PUBLICATIONS

Ha, Chang Hoon; et al; "Novel mechanism of gene transfection by low-energy shock wave" Scientific Reports, 5, 12843, 2015 (Year: 2015).*
Mariotto, Sofia; et al; "Extracorporeal shock waves: From lithotripsy to anti-inflammatory action by NO production" Nitric Oxide, 12, 89-96, 2005 (Year: 2005).*
Holfeld, Johannes; et al; "Shock Wave Application to Cell Cultures" Journal of Visualized Experiments, 86, e51076, 2014 (Year: 2014).*
Boon, "Endothelial microRNA tells smooth muscle cells to proliferate," *Circulation Research* 113: 7-8 (Jun. 21, 2013).
Chaussy et al., "First clinical experience with extracorporeally induced destruction of kidney stones by shock waves," *Journal of Urology* 167: 844-847 (Feb. 2002).

* cited by examiner

*Primary Examiner* — David W Berke-Schlessel
(74) *Attorney, Agent, or Firm* — Klarquist Sparkman, LLP

(57) ABSTRACT

The present invention relates to a method for promoting the generation and secretion of extracellular vesicles from cells by using extracorporeal shockwave. More precisely, the inventors confirmed that the generation and secretion of extracellular vesicles from vascular endothelial cells were promoted by extracorporeal shockwave and further confirmed that siRNA can be transferred into cells without any help of a carrier. The inventors continued to find out that angiogenesis could be inhibited by introducing siRNA to an animal tumor model and succeeded to measure the size and amount of extracellular vesicles secreted by extracorporeal shockwave. Therefore, the present invention can be used in various fields since it can safely promote the generation and secretion of extracellular vesicles from cells.

12 Claims, 29 Drawing Sheets
(13 of 29 Drawing Sheet(s) Filed in Color)
Specification includes a Sequence Listing.

SW 0.04 / 1,000s / 3min

Control    si VEGFR-2

IB: VEGFR2

IB: beta-actin

Control    si VE-cadherin

IB: VE-cadherin

IB: beta-actin

SEQUENCE LISTING

```
<160> NUMBER OF SEQ ID NOS: 4

<210> SEQ ID NO 1
<211> LENGTH: 25
<212> TYPE: RNA
<213> ORGANISM: Homo sapiens

<400> SEQUENCE: 1
acaaugacua uaagacaugc uaugg                                        25

<210> SEQ ID NO 2
<211> LENGTH: 27
<212> TYPE: RNA
<213> ORGANISM: Homo sapiens

<400> SEQUENCE: 2
ccauagcaug ucuuauaguc auuguuc                                      27
```

```
<210> SEQ ID NO 3
<211> LENGTH: 25
<212> TYPE: RNA
<213> ORGANISM: Homo sapiens

<400> SEQUENCE: 3
gcaauagaca aggacauaac accac                                              25

<210> SEQ ID NO 4
<211> LENGTH: 27
<212> TYPE: RNA
<213> ORGANISM: Homo sapiens

<400> SEQUENCE: 4
gugguguuau guccuugucu auugcgg                                            27
```

METHOD FOR SECRETION OF EXTRACELLULAR VESICLES FROM CELLS AND TISSUES USING SHOCK WAVE

CROSS REFERENCE TO RELATED APPLICATIONS

This application claims priority under 35 U.S.C. § 120 to Korean Patent Application No. 10-2016-0006974 filed on Jan. 20, 2016, which is here in incorporated by reference in its entirety.

BACKGROUND

1. Field

The present invention relates to a method for promoting the generation and secretion of extracellular vesicles from cells using extracorporeal shockwave, and thereby the invention can be applied to various studies and treatments because it is not harmful for cells and tissues and can only promote the generation and secretion of extracellular vesicles.

2. Description of the Related Art

Shockwave is a continuous single sound wave generated by a specific sound wave generator, having high peak pressure amplitude of up to 100 MPa and a short duration of less than 1 μm. The shockwave can be delivered to a specific target area with an energy density in the range of 0.005~0.32 mJ/mm$^2$.

High-energy extracorporeal shock-wave lithotripsy is a kind of treatment method for breaking stones in the kidney and bile duct by applying pressure of 35 to 100 MPa to the target area of human body. This method has been attempted as a new treatment method in a variety of fields since it was first tried (Chaussy, C. et al. First clinical experience with extracorporeally induced destruction of kidney stones by shock waves. *J Urol* 127, 417.420 (1982)). Recently, it has been reported that extracorporeal shock-wave lithotripsy is used in the treatment of musculoskeletal diseases and is effective for anti-inflammatory action and blood flow increase.

Extracellular vesicles are the microscopic particles secreted by cells in the size of a few nm~a few μm. In the past, they were regarded as debris secreted from the cells, but they are now considered clinically meaningful. Therefore, various studies about the extracellular vesicles are actively going on. In particular, exosomes, the spherical follicles released by cells, have lots of information about the mother cell protein and DNA, etc. So, it has been attempted to develop a marker and a sensor to detect cancer by using the same as a bio-marker.

Thus, the present inventors have been studying methods for promoting the generation and secretion of extracellular vesicles including exosomes, ectosomes, microvesicles, or apoptotic bodies. In the course of our study, the inventors confirmed that the generation and secretion of extracellular vesicles were increased in the cells treated with extracorporeal shockwave and accordingly established a method to mass-produce extracellular vesicles including target DNA or RNA, leading to the completion of the invention.

SUMMARY OF THE INVENTION

It is an object of the present invention to provide a method for promoting the generation and secretion of extracellular vesicles from cells by using extracorporeal shockwave.

To achieve the above object, the present invention provides a method for promoting the secretion of extracellular vesicles from cells containing the step of treating extracorporeal shockwave to cells or a subject except human.

The present invention also provides a method for producing extracellular vesicles including one or more materials selected from the group consisting of nucleic acids, proteins, and compounds, containing the step of treating extracorporeal shockwave to cells.

Advantageous Effect

The present invention relates to a method for promoting the generation and secretion of extracellular vesicles from the cells using shockwave. More precisely, the present inventors confirmed that the generation and secretion of extracellular vesicles from vascular endothelial cells were increased by extracorporeal shockwave and the insertion of such materials as siRNA into cells or animal models was easy by using the said extracellular vesicles. Therefore, the method of the present invention is a safe method to promote the generation and secretion of extracellular vesicles containing nucleic acids, proteins, or compounds from cells or a subject except human, and thus it can be applied to various fields.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The application of the preferred embodiments of the present invention is best understood with reference to the accompanying drawings, wherein:

FIG. 2A is a diagram illustrating the expression of VEGFR2 in the HUVECs transfected with VEGFR2 siRNA by using extracorporeal shockwave or Lipofectamine;

FIG. 2B is a diagram illustrating the numerical expression of FIG. 2A;

FIG. 2C is a diagram illustrating the confirmation of the transfection of HUVECs using extracorporeal shockwave or Lipofectamine by adding a fluorescent material to the culture medium of HUVECs;

FIG. 2D is a diagram illustrating the confirmation of the transfection of HUVECs with Cy3-labeled VEGFR2 siRNA by using extracorporeal shockwave or Lipofectamine.

cells with Cy3-labeled GAPDH siRNA by using extracorporeal shockwave or Lipofectamine.

Figure 7:
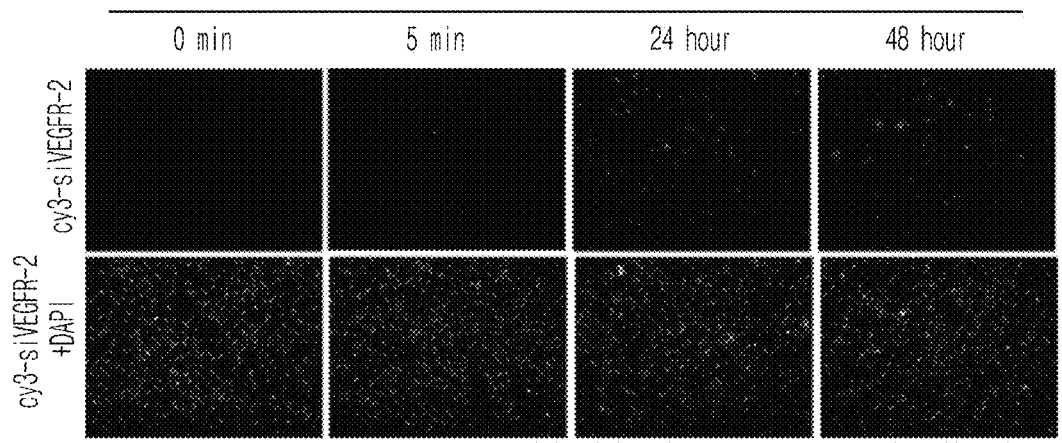
Figure 7:
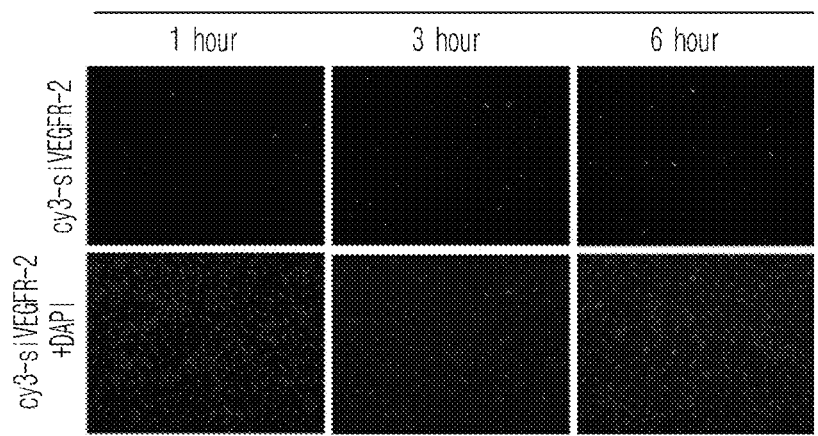

FIG. 7 is a diagram illustrating the transfection efficiency after the extracorporeal shockwave treatment according to the culture time.

Figure 8A:
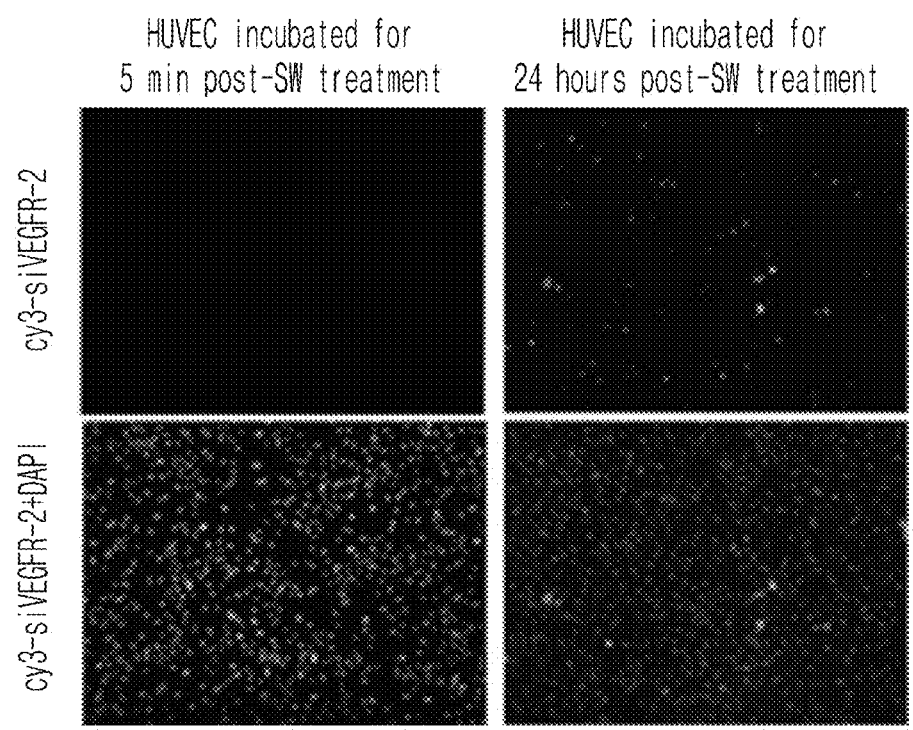
Figure 8B:
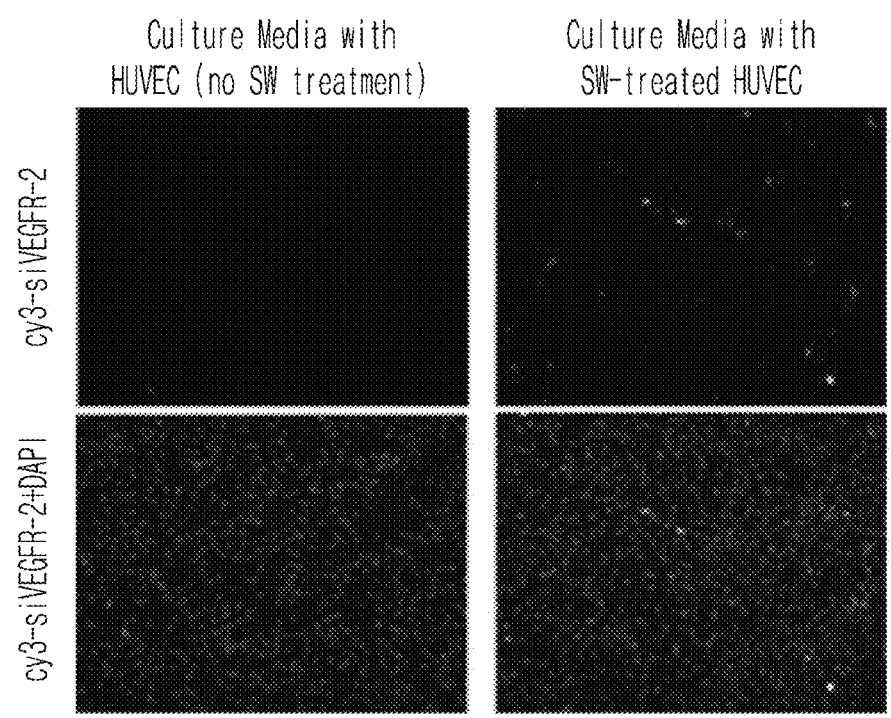
Figure 8C:
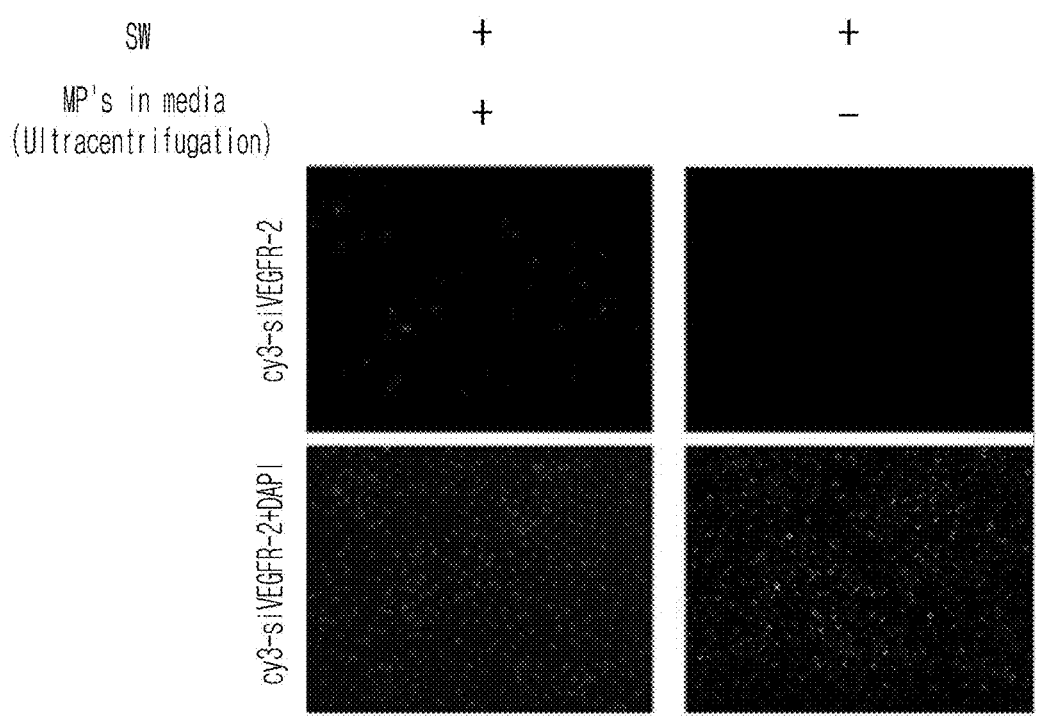

FIGS. 8A-8C is a set of diagrams illustrating the transfection efficiency after the extracorporeal shockwave treatment according to the culture time or conditions;

FIG. 8A is a diagram illustrating the transfection efficiency when HUVECs were treated with Cy3-labeled siRNA and extracorporeal shockwave, cultured for a certain period of time (5 minutes and 24 hours), and then transferred in a siRNA-free medium, followed by further culture for 24 hours;

FIG. 8B is a diagram illustrating the transfection efficiency when the Cy3-labeled siRNA treated HUVECs were treated or non-treated with extracorporeal shockwave, and then transferred in a medium not treated with extracorporeal, followed by culture;

FIG. 8C is a diagram illustrating the transfection efficiency when HUVECs were transfected with Cy3-labeled siRNA and extracorporeal shockwave and the extracellular vesicles were eliminated from the medium, followed by further culture.

Figure 9A:
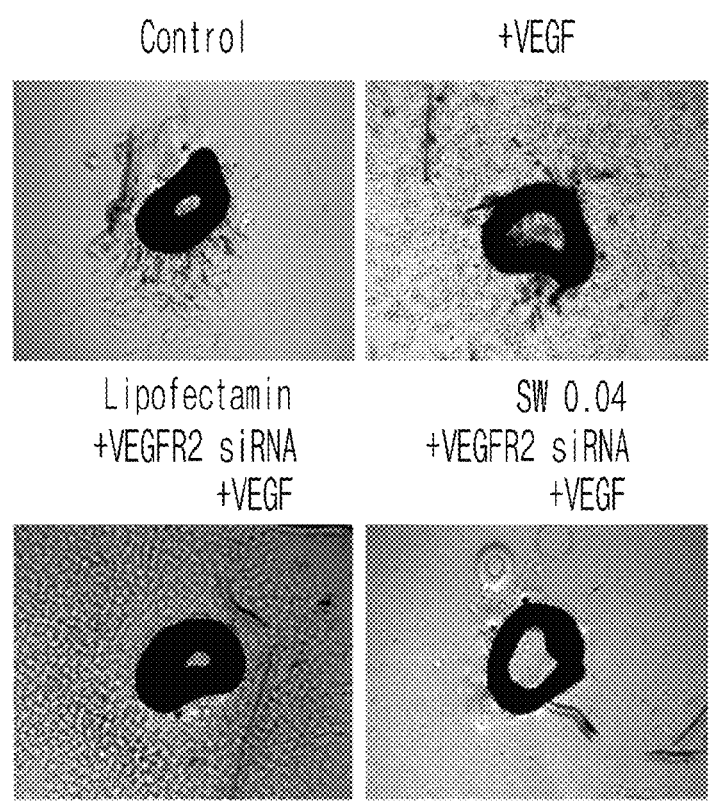
Figure 9B:
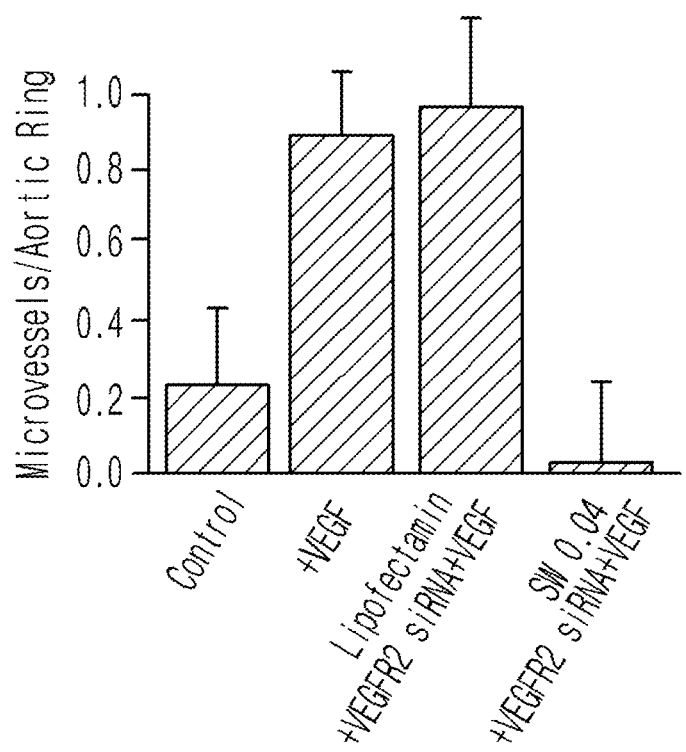

FIGS. 9A-9B is a set of diagrams illustrating the transfection effect of extracorporeal shockwave ex vivo;

FIG. 9A is a diagram illustrating the angiogenesis in the mouse aortic ring transfected with VEGFR2 siRNA by using extracorporeal shockwave or Lipofectamine;

FIG. 9B is a diagram illustrating the schematization of FIG. 9A.

Figure 10A:
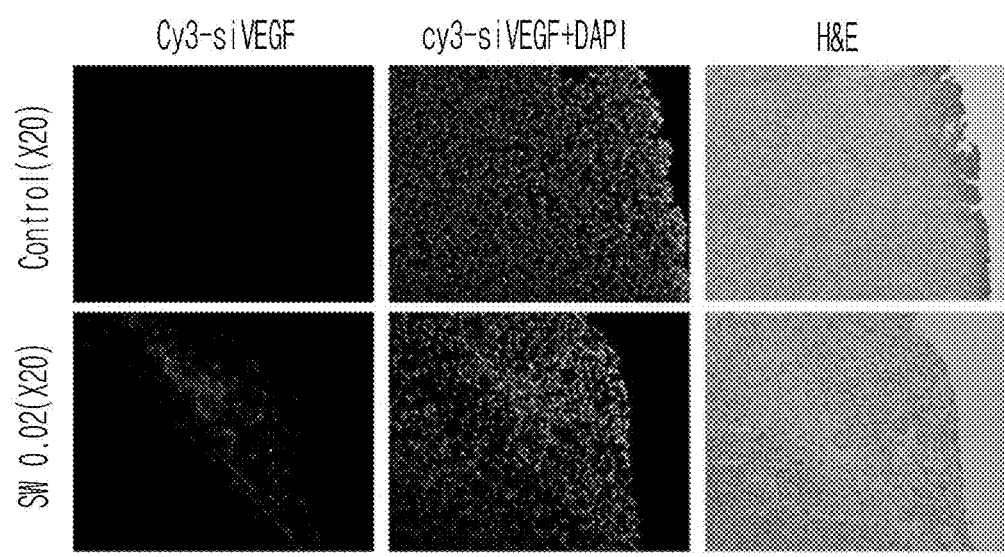
Figure 10B:
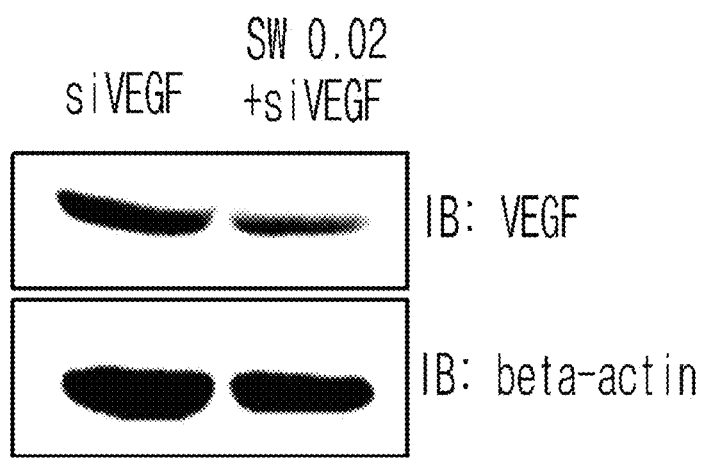
Figure 10C:
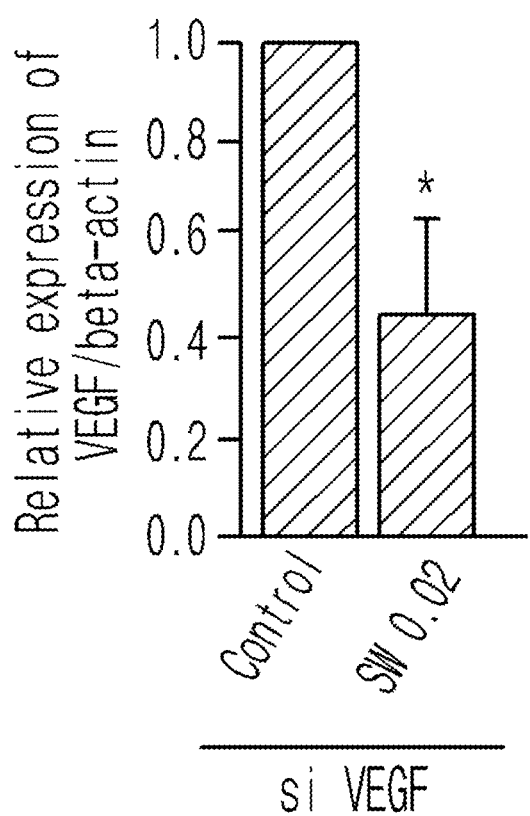
Figure 10D:
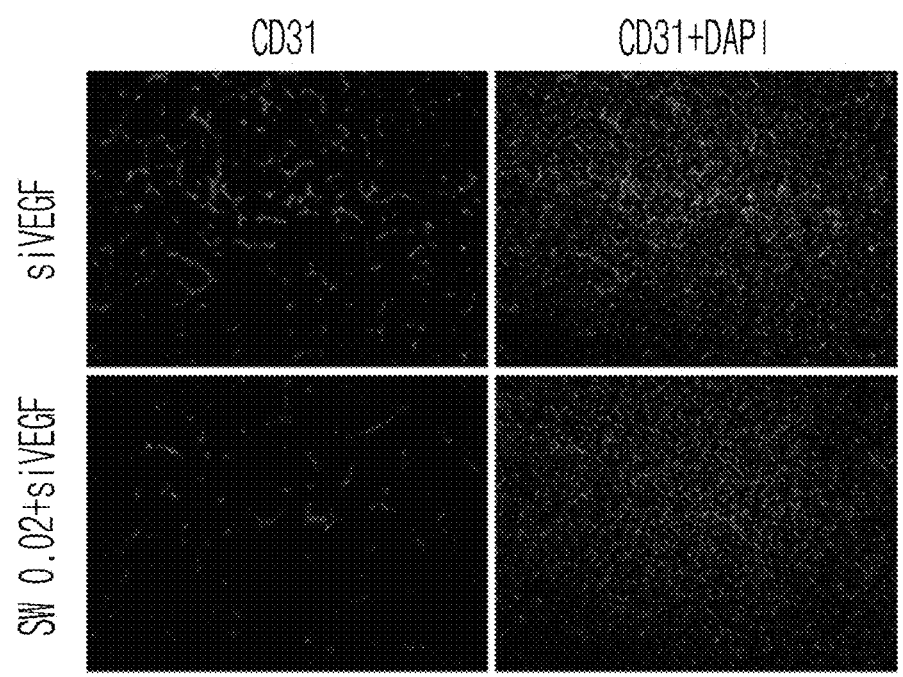
Figure 10E:
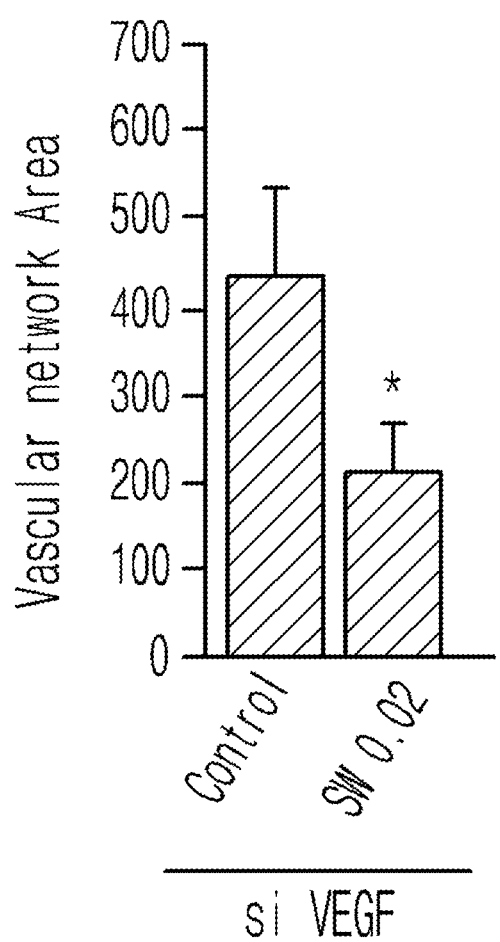

FIGS. 10A-10E is a set of diagrams illustrating the CT26 tumor treatment effect of the siRNA transfection induced by extracorporeal shockwave;

FIG. 10A is a diagram illustrating the transfection of the CT26 tumor mouse model with Cy3-labeled VEGF siRNA by using extracorporeal shockwave;

FIGS. 10B and 10C are diagrams illustrating the expression of VEGF in the CT26 tumor model after the transfection using VEFG siRNA and extracorporeal shockwave;

FIGS. 10D and 10E are diagrams illustrating the expression of CD31 in the CT26 tumor model after the transfection using extracorporeal shockwave.

Figure 11:
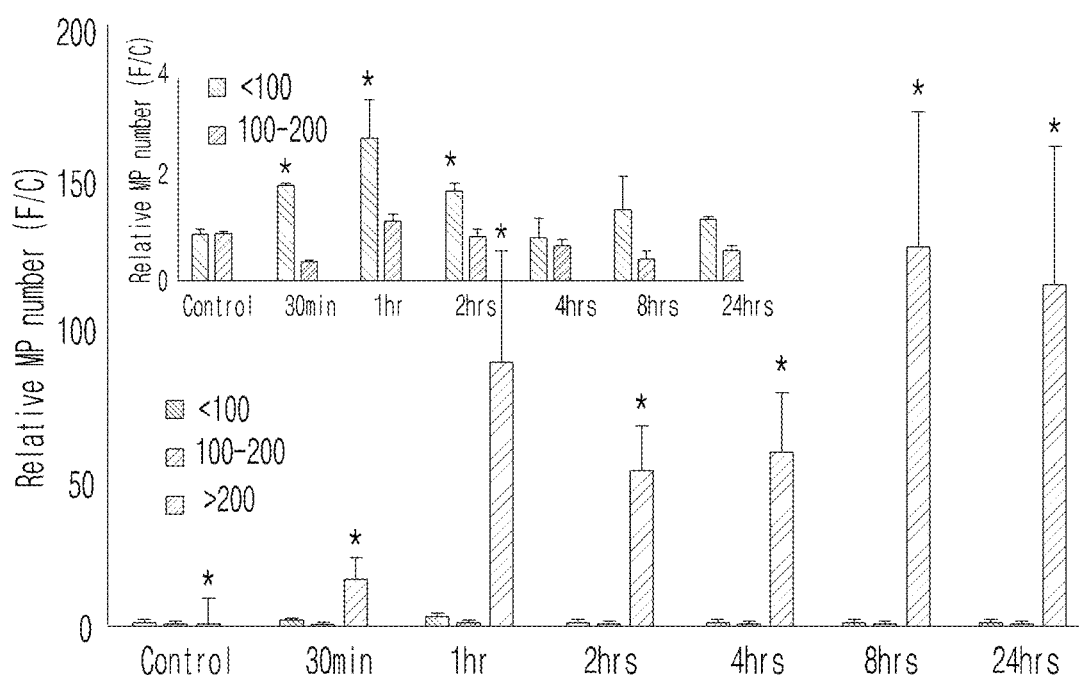

FIG. 11 is a diagram illustrating the results of NTA (nanoparticle tracking analysis) examining the changes of extracellular vesicles after the transfection using extracorporeal shockwave.

Figure 12A:
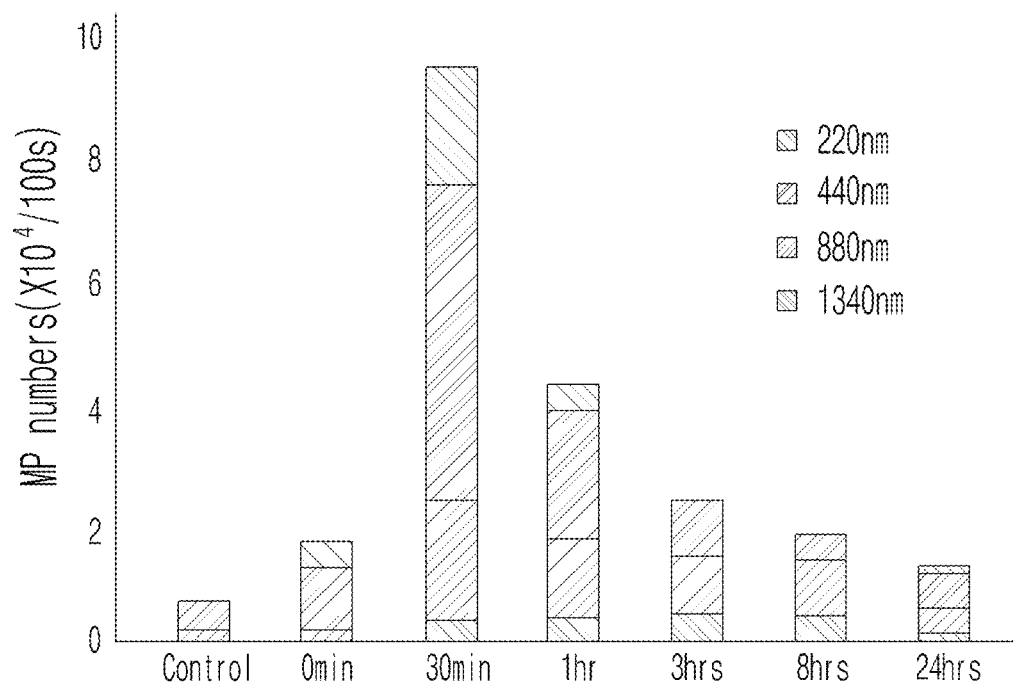
Figure 12B:
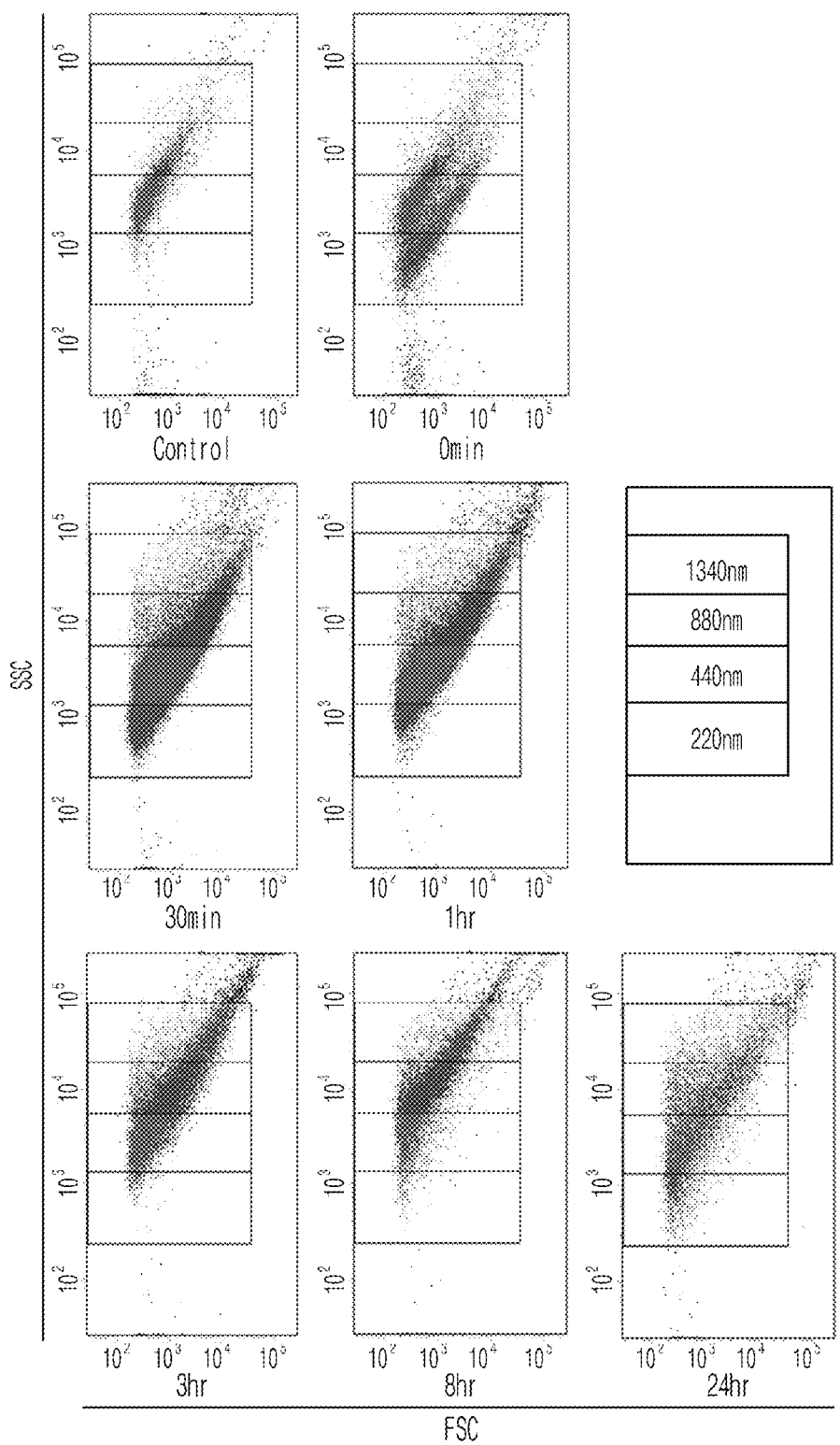

FIGS. 12A-12B are diagrams illustrating the results of FACS examining the distribution of extracellular vesicles after the transfection using extracorporeal shockwave.

Figure 13A:
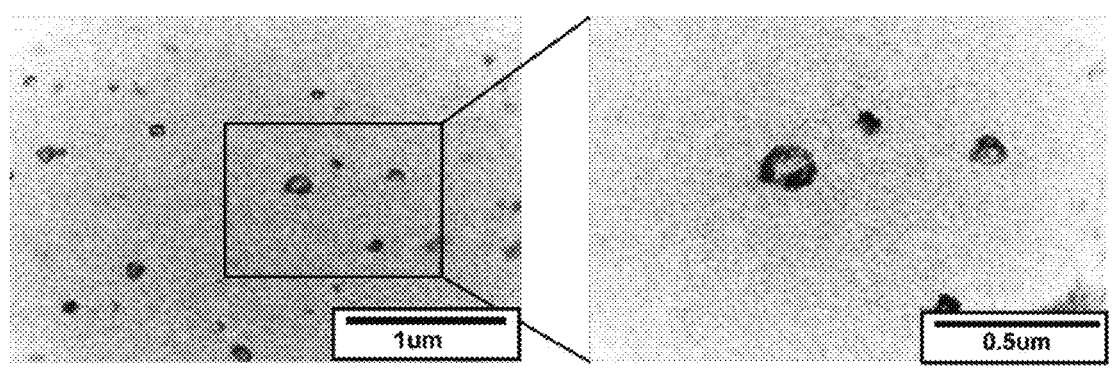
Figure 13B:
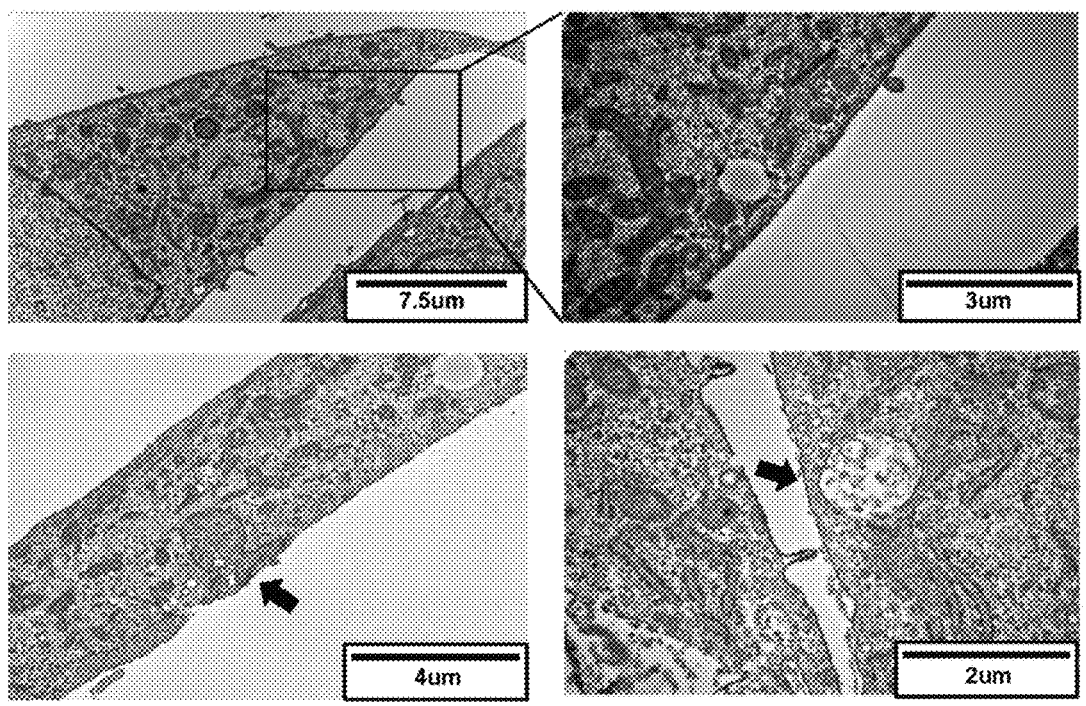

FIGS. 13A-13B. FIG. 13A is a diagram illustrating the extracellular vesicles in the medium and cell pellets, observed under TEM (transmission electron microscope).

FIG. 13B is a picture illustrating the extracellular vesicles in the cytoplasm large particle, observed under TEM.

Figure 14A:
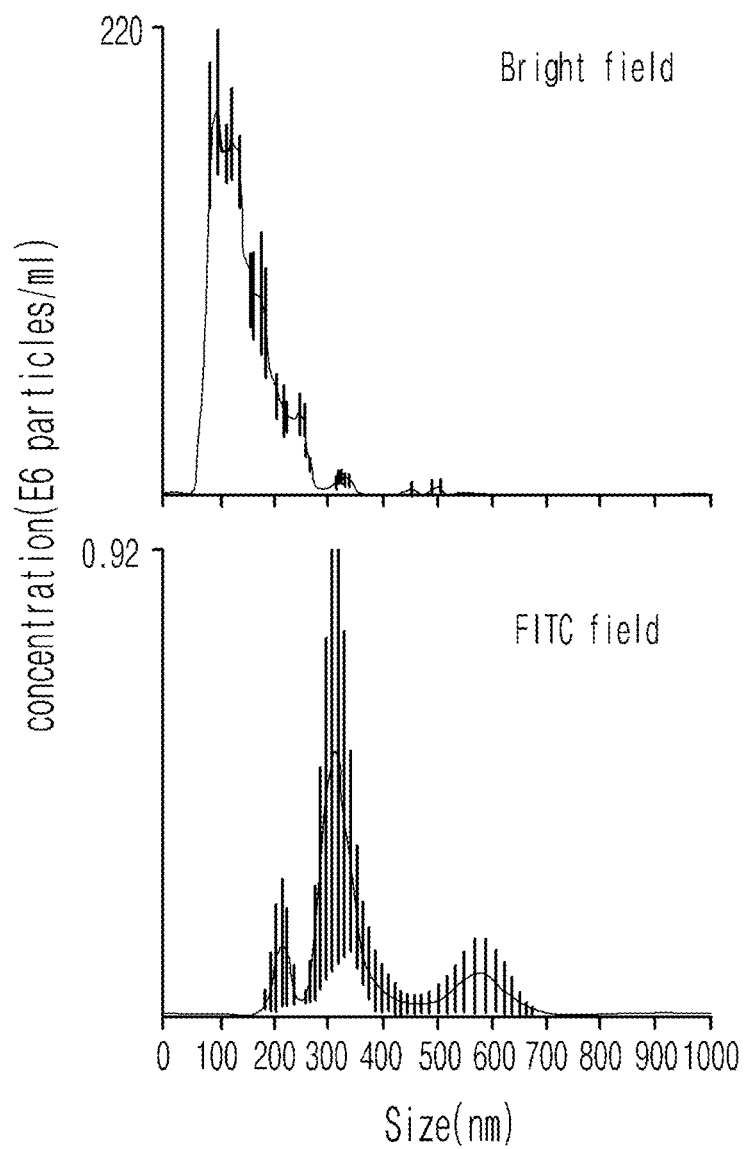
Figure 14B:
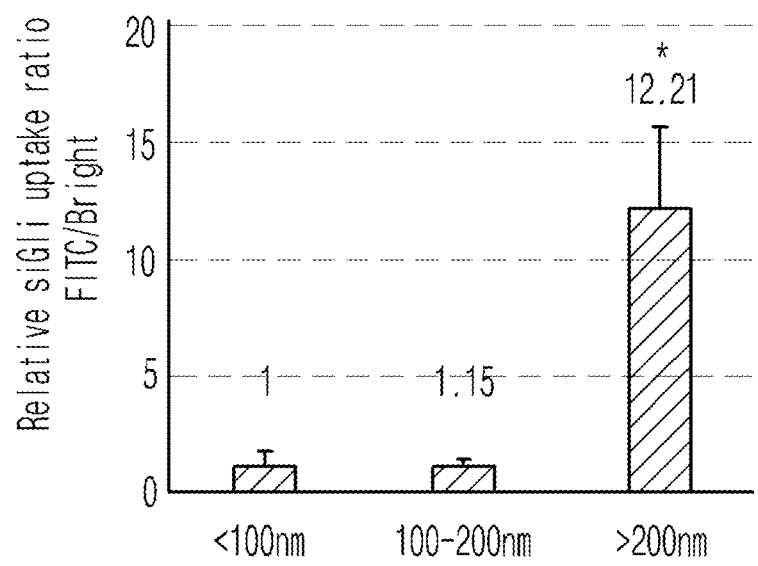

FIGS. 14A-14B are diagrams illustrating the secretion of extracellular vesicles after the transfection using extracorporeal shockwave.

SEQUENCE LISTING

The Sequence Listing is submitted as an ASCII text file [7037-98293-01_Sequence_Listing.txt, Jan. 18, 2017, 941 bytes], which is incorporated by reference herein.

DESCRIPTION OF THE PREFERRED EMBODIMENTS

Hereinafter, the term used in this invention is described in more detail.

The term "extracellular vesicle" in this invention indicates a small sphere surrounded by a membrane originated from cells. This sphere varies greatly depending on the origins of the cells in which it is made or the way it is made. In this invention, the sphere includes any one selected from the group consisting of exosome, ectosome, microvesicle, and apoptotic body, which had been named according to the method of making in cells.

Hereinafter, the present invention is described in detail.

The present invention provides a method for promoting the secretion of extracellular vesicles from cells containing the step of treating extracorporeal shockwave to cells or a subject except human.

The extracorporeal shockwave above is preferably treated in the energy range of 0.01~1.0 $mJ/mm^2$, more preferably in the energy range of 0.01~0.06 $mJ/mm^2$, and most preferably in the energy range of 0.02~0.04 $mJ/mm^2$. The energy greater than 0.09 $mJ/mm^2$ would induce cell death, so that the secretion of extracellular vesicles would be rather inhibited.

The cells herein are preferably isolated from a subject. The cells can be originated from any type of animal including human and non-human mammals, and can be various types of immune cells, tumor cells, etc, but not always limited thereto. In a preferred embodiment of the invention, the cells above are preferably HUVECs (human umbilical vein endothelial cells) separated from human umbilical veins and HSMC, human smooth muscle cells (HSMCs), murine colon adenocarcinoma cells (CT26), human prostate cancer cell line (PC-3), immortalized mouse aortic endothelial cells (iMAEC), or monkey kidney fibroblast cells (COS-7).

The extracellular vesicles above can be selected from the group consisting of exosomes, ectosomes, microvesicles, and apoptotic bodies.

In a preferred embodiment of the present invention, the present inventors confirmed that the generation and secretion of extracellular vesicles were increased in vascular endothelial cells and siRNA could migrate into the cells for the transfection (see FIGS. 1, 2 and 3) when extracorporeal shockwave was treated thereto. This effect was as excellent as or better than that of lipofectamine (see FIG. 2).

It was confirmed that the generation and secretion of extracellular vesicles were increased and siRNA migrated into the cells to induce transformation when various cell lines were treated with extracorporeal shockwave (see FIG. 2 and FIGS. 4, 5 and 6).

It was also confirmed that the transfection effect by extracorporeal shockwave was not through the pores on the cell membrane as known previously (see FIGS. 7 and 8). It was further confirmed that angiogenesis was inhibited when siRNA was introduced by using extracorporeal shockwave in an animal tumor model (see FIGS. 9 and 10).

The present inventors also confirmed that the secretion of extracellular vesicles induced by extracorporeal shockwave via NTA and FACS (see FIGS. 11-14). Therefore, the method of the invention can be effectively used for the promotion of the generation and secretion of extracellular vesicles from cells.

The present invention also provides a method for producing extracellular vesicles including one or more materials selected from the group consisting of nucleic acids, proteins, and compounds, containing the step of treating extracorporeal shockwave to cells.

The present invention also provides the extracellular vesicles produced by the method of the invention above.

The extracorporeal shockwave above is preferably treated in the energy range of 0.01~1.0 $mJ/mm^2$, and more preferably in the energy range of 0.02~0.04 $mJ/mm^2$.

The extracellular vesicles above can be selected from the group consisting of exosomes, ectosomes, microvesicles, and apoptotic bodies.

The nucleic acid herein is any of DNA, RNA, microRNA, small interfering RNA(siRNA), small nucleolar RNA(snoRNA) and long non-coding RNA(lncRNA), and particularly in a preferred embodiment of the present invention, it is preferably DNA or RNA.

In a preferred embodiment of the present invention, the inventors confirmed that the treatment of extracorporeal shockwave increased the generation and secretion of extracellular vesicles in vascular endothelial cells and induced the migration of siRNA into cells for the transformation thereof (see FIGS. 1~3), and such effect was equally observed in various cell lines (see FIG. 2, and FIGS. 4-6). Therefore, the method of the invention can be effectively used for the production of extracellular vesicles containing target DNA and RNA.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Cell Culture and Extracorporeal Shockwave Treatment

HUVECs (human umbilical vein endothelial cell) were separated from human umbilical veins. HSMCs were purchased from Gibco (Inchinnan, Scotland, UK). HUVECs and HSMCs were cultured in Medium 200 supplemented with 5% fetal bovine serum (FBS) and low-serum growth supplement (LSGS; Cascade Biologics Inc., Winchester, Mass., USA). The FBS containing extracellular vesicles was centrifuged at 170,000×g for 2 hours to eliminate all the extracellular vesicles. Immortalized mouse aortic endothelial cells (iMAECs) were provided from Dr. Hanjoong Jo (Emory University, Atlanta, Ga., USA) and cultured in DMEM (Dulbecco's Modified Eagle Medium) supplemented with 10% FBS, 1% penicillin-streptomycin, 50 μg/ml of growth supplement (Sigma Aldrich, St. Louis, Mo., USA), and non-essential amino acids.

To treat extracorporeal shockwave to the cells in vitro, the cells were cultured in a 12-well plate and then extracorporeal shockwave was treated thereto by using Dornier AR2 ESWT (Dornier MedTech, Germany). Briefly, the treatment of extracorporeal shockwave was performed by allowing a sterile extracorporeal shockwave probe to contact the surface of the medium perpendicularly to the well plate. The gap between the extracorporeal shockwave probe and the cell layer of the bottom of the plate was 1.2 cm. The cultured cells were exposed on 1,000 shots of extracorporeal shockwave in a designated energy level for 3 minutes, followed by culture in a 37° C. $CO_2$ incubator.

Experimental Example 1: Transfection Effect of Extracorporeal Shockwave at a Low Energy Level in Endothelial Cells To develop an extracorporeal shock wave (SW) induced gene delivery system, a single-sonic generator (Dornier MedTech, Wessling, Germany) generating fixed electromagnetic shockwave at a diameter of 1 cm and a depth of 4 cm was used. At low energy levels of 0.01~0.04 $mJ/mm^2$, HUVECs (human umbilical vein endothelial cells) were not affected. However, at energy levels of higher than 0.09 $mJ/mm^2$, high killing effect was observed. Therefore, it was considered that the treatment of extracorporeal shockwave at 0.04 $mJ/mm^2$ was effective in transfecting the primary cultured cells with siRNA, and that energy level was regarded as a safe energy level.

First, the effect of extracorporeal shockwave on the transfection of HUVECs with siRNA was investigated in vitro.

Particularly, siRNAs targeting VEGFR2, VE-cadherin (vascular endothelial-cadherin), and GAPDH, and scrambled siRNA (control) were purchased from Integrated DNA Technologies (IDT; Coralville, Iowa, USA).

Human VEGFR2 and VE-cadherin siRNA sequences are as shown in Table 1 below.

TABLE 1

| Gene | | siRNA sequence |
|---|---|---|
| Human VEGFR2 | sense | 5'-ACAAUGACUAUAAGACAUGCUAUGG (SEQ. ID. NO: 1) |
| | antisense | 5'-CCAUAGCAUGUCUUAUAGUCAUUGUUC (SEQ. ID. NO: 2) |
| Human VE-cadherin | sense | 5'-GCAAUAGACAAGGACAUAACACCAC (SEQ. ID. NO: 3) |
| | antisense | 5'-GUGGUGUUAUGUCCUUGUCUAUUGCGG (SEQ. ID. NO: 4) |

Cells were cultured in a 6-well plate for 24 hours until the confluence reached 80%. Then, siRNA was added to the culture medium, which was treated with 1,000 shots extracorporeal shockwave at 0.04 $mJ/mm^2$ for 3 minutes. Then the cells were cultured at 37° C. 24 hours after the extracorporeal shockwave treatment, the cells were harvested. Lipofectamine 2000 (Invitrogen, Waltham, Mass., USA) was used as the positive control for the siRNA transfection. The experiment was performed according to the conventional method well informed to those in the art (Wong, C. & Jin, Z. G. Protein kinase C-dependent protein kinase D activation modulates ERK signal pathway and endothelial cell proliferation by vascular endothelial growth factor. *J Biol Chem* 280, 33262.33269 (2005)).

The effect on the transfection was examined by SDS-PAGE, Western blotting, and immunofluorescent analysis with the obtained cells.

Particularly, the transfected cells were collected by using the lysis buffer (0.5% Triton X-100, 0.5% Nonidet P-40, 10 mM Tris, pH 7.5, 2.5 mM KCl, 150 mM NaCl, 30 mM glycerophosphate, 50 mM NaF, and 1 mM $Na_3VO_4$) containing 0.1% protease inhibitor mixture (Sigma), followed by centrifugation. Then, the concentration of the lysate was measured by Bradford method (Bio-Rad, Hercules, Calif., USA). The protein complex was separated by SDS-PAGE (sodium dodecyl sulfate polyacrylamide gel electrophoresis), and then transferred onto nitrocellulose membranes. The membrane was incubated with the primary antibody, which was then washed, followed by further incubation with the secondary antibody. Anti-VEGF, VEGFR-2, and VE-cadherin (C-19) antibodies were purchased from Cell Signaling Technologies (Beverly, Mass., USA). Anti-β-actin and GAPDH antibodies were purchased from Santa Cruz Biotechnology (Dallas, Tex., USA). The immunoreactive protein was visualized by using ECL (enhanced chemiluminescence) detection system (Amersham Biosciences, Amersham, UK). Some membranes were stripped and conjugated with another antibody.

The concentration of the immunoblot was analyzed using ImageJ software (National Institutes of Health), and the results were standardized by setting the cells of the control group to '1.0'.

Figure 1:
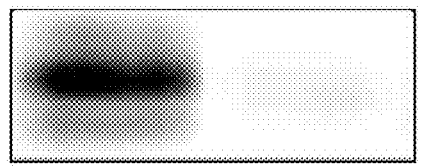
FIG. 1 is a diagram illustrating the transfection of HUVECs (human umbilical vein endothelial cells) with VEGFR2 siRNA and VE-cadherin siRNA by using extracorporeal shockwave.
Figure 1:
Figure 1:
Figure 1:
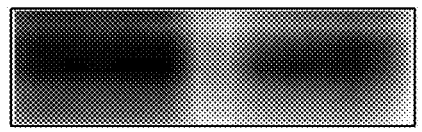

Cells were transfected with Cy3-labeled VEGFR2 siRNA, followed by immunofluorescent staining. As a result, as shown in FIG. 1, the expressions of VEGFR2 and VE-cadherin were significantly reduced in the HUVECs transfected with siRNA targeting VEGFR2 and VE-cadherin after the treatment of extracorporeal shockwave (0.04 mJ/mm$^2$). This result indicates that the siRNA transfection in the primary cultured cells was induced by extracorporeal shockwave (FIG. 1).

Figure 2A:
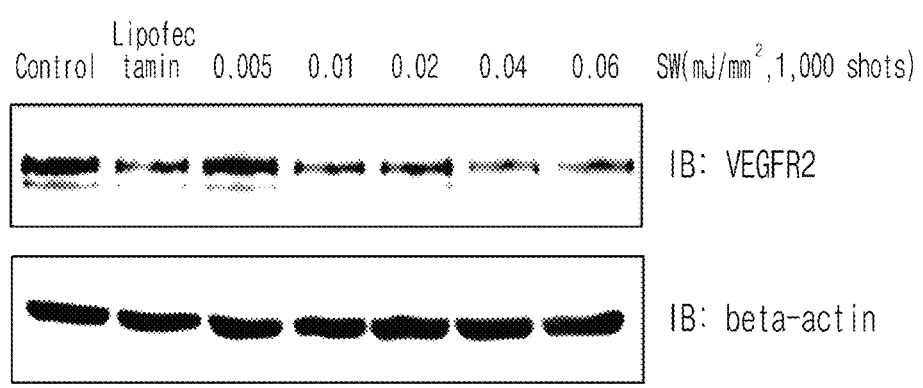
FIGS. 2A-2D is a set of diagrams illustrating the transfection of HUVECs with VEGFR2 siRNA by using extracorporeal shockwave or lipofectamine.
Figure 2B:
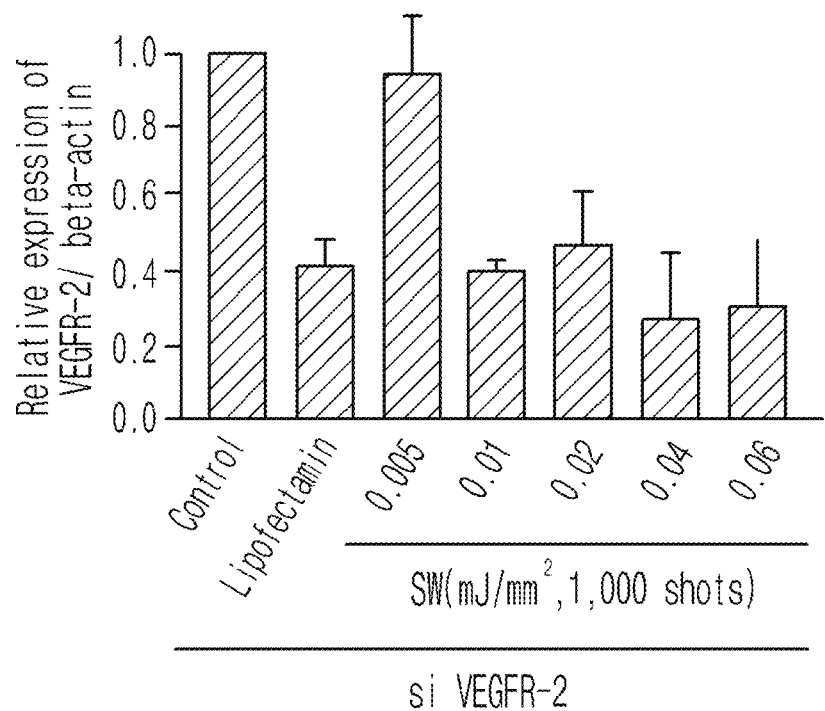
Figure 2C:
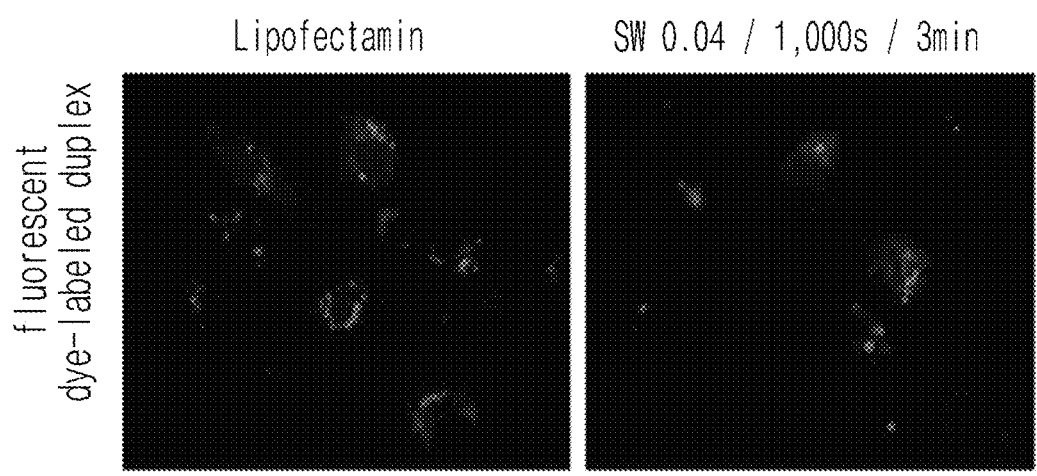
Figure 2D:
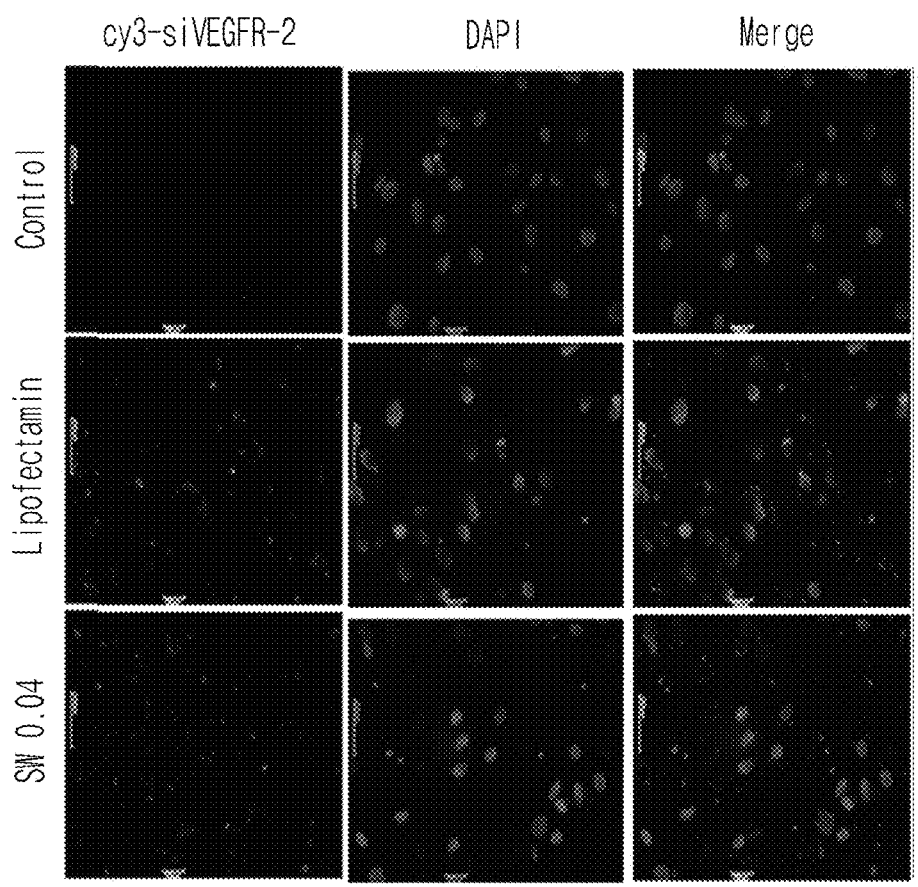

Next, the transfection efficiency of extracorporeal shockwave was compared with that of lipofectamine. As shown in FIGS. 2A and 2B, VEGFR2 siRNA was introduced in HUVECs when extracorporeal shockwave was treated at the energy levels of 0.02~0.06 mJ/mm$^2$, and the Cy3-labeled VEGFR2 siRNA transfection efficiency of extracorporeal shockwave was similar to that of lipofectamine (FIG. 2).

To investigate the transfection efficiency of the plasmid induced by extracorporeal shockwave, HUVECs were transfected with the vector encoding full-length eGFP (enhanced green fluorescence protein) by using extracorporeal shockwave (0.04 mJ/mm$^2$) or lipofectamine.

Figure 3:
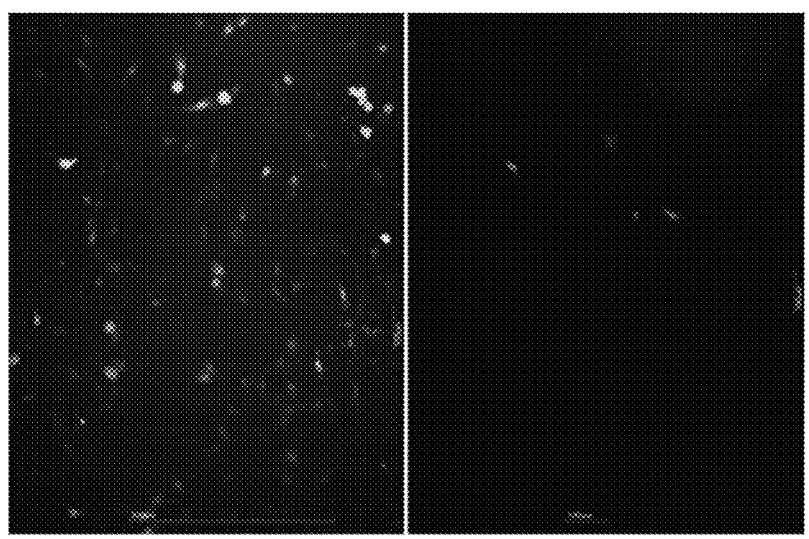
FIG. 3 is a diagram illustrating the transfection of HUVECs with a vector encoding GFP (green fluorescent protein) by using extracorporeal shockwave or Lipofectamine.

As a result, as shown in FIG. 3, the transfection efficiency was high in the group treated with lipofectamine and the GFP-positive cells were increased therein. In the meantime, the GFP-positive cells were less in the group treated with extracorporeal shockwave (FIG. 3). This result indicates that the transfection efficiency with plasmid could be lowered by the treatment of extracorporeal shockwave.

Experimental Example 2: Confirmation of Extracorporeal Shockwave-Induced siRNA Delivery Efficiency in Various Cell Lines To investigate the gene silencing effect in the various cell lines transfected with siRNA using extracorporeal shockwave, HSMCs (human smooth muscle cells) and murine colon adenocarcinoma cells (CT26) were transfected with Cy3-labeled GAPDH siRNA by using extracorporeal shockwave (0.04 mJ/mm$^2$) or lipofectamine.

Particularly, transfection, SDS-PAGE, Western blotting, and immunofluorescent staining were performed by the same manner as described in Experimental Example 1.

Figure 4:
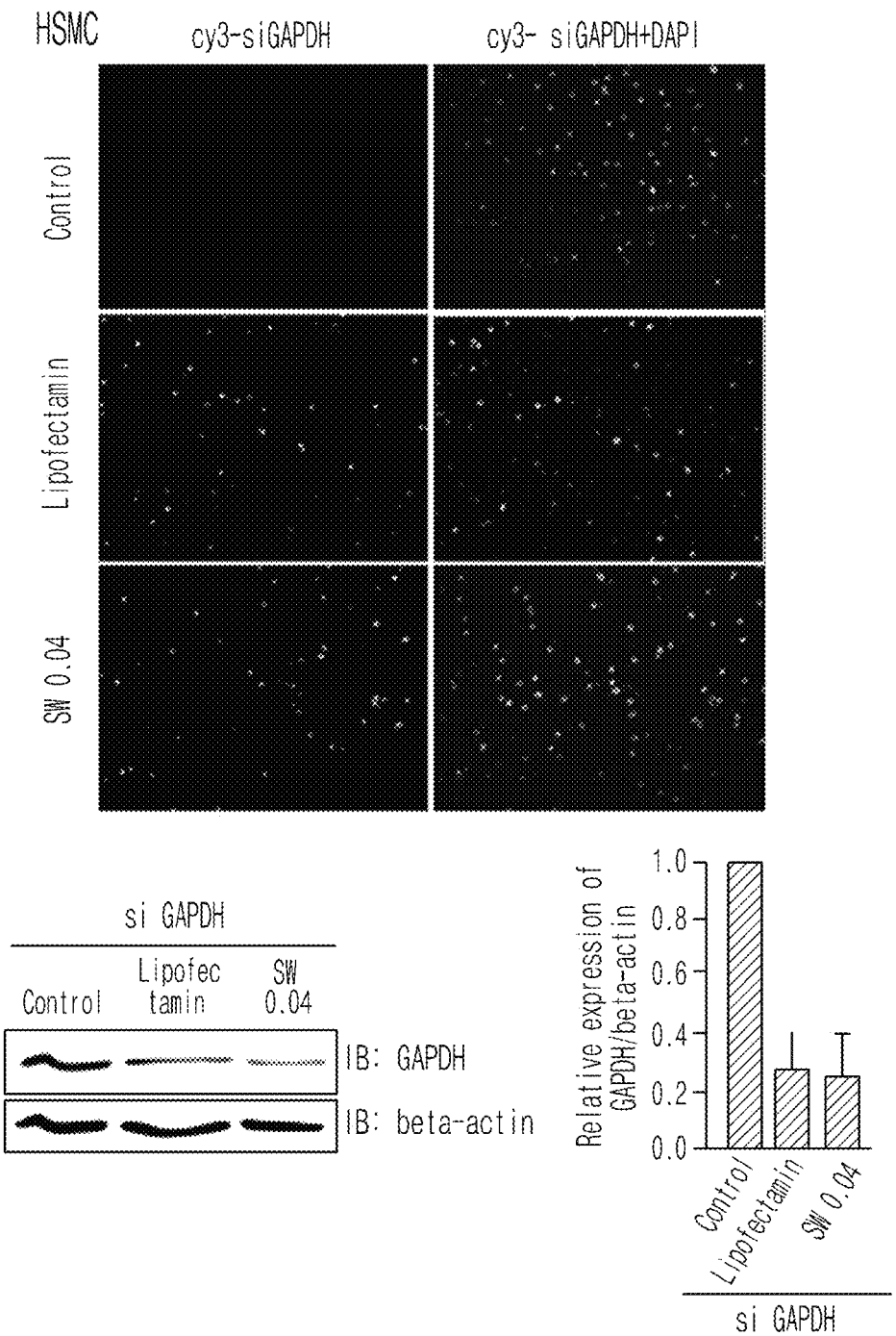
FIG. 4 is a diagram illustrating the transfection of human smooth muscle cells (HSMCs) with Cy3-labeled GAPDH siRNA by using extracorporeal shockwave or Lipofectamine.
Figure 5:
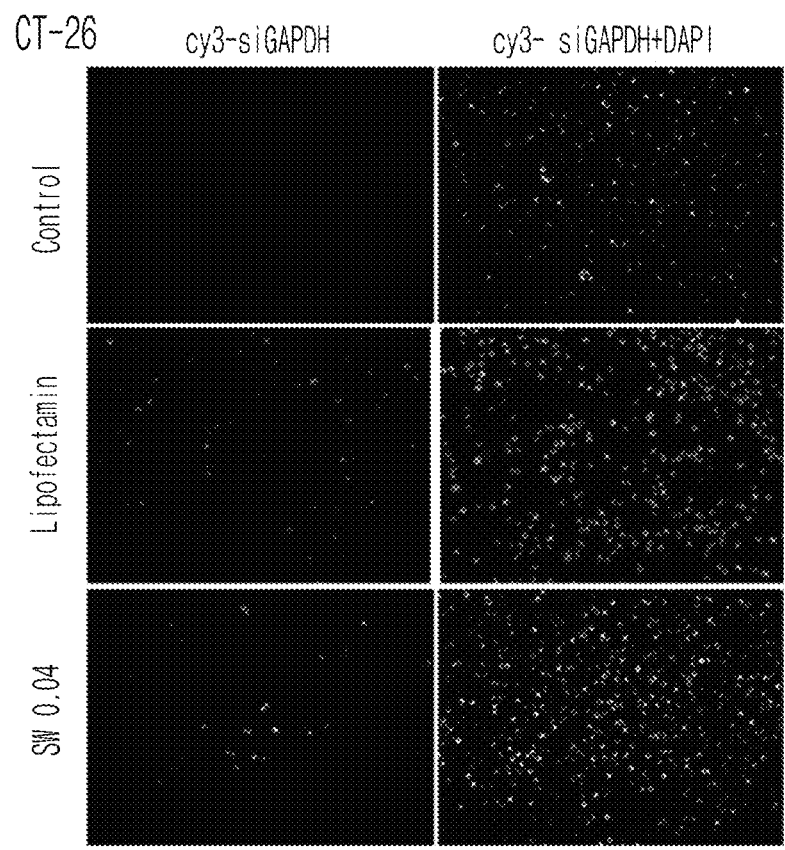
FIG. 5 is a diagram illustrating the transfection of CT-26 cells with Cy3-labeled GAPDH siRNA by using extracorporeal shockwave or Lipofectamine.
Figure 5:
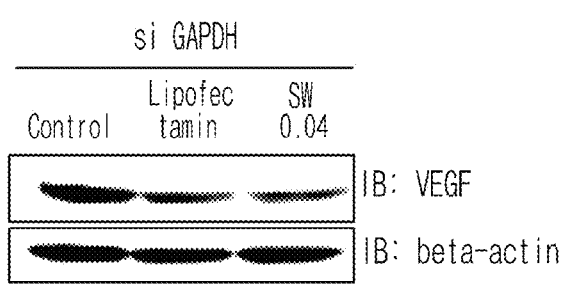
Figure 5:
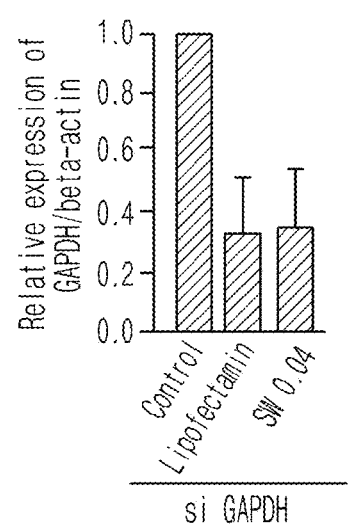

As a result, as shown in FIGS. 4 and 5, 24 hours after the extracorporeal shockwave treatment, the transfection efficiency in HSMCs and CT26 was similar to that of the group treated with lipofectamine (FIGS. 4 and 5). In the meantime, the expression of GAPDH was significantly lowered when GAPDH siRNA was transfected by extracorporeal shockwave, compared with the control ($p<0.05$).

Figure 6A:
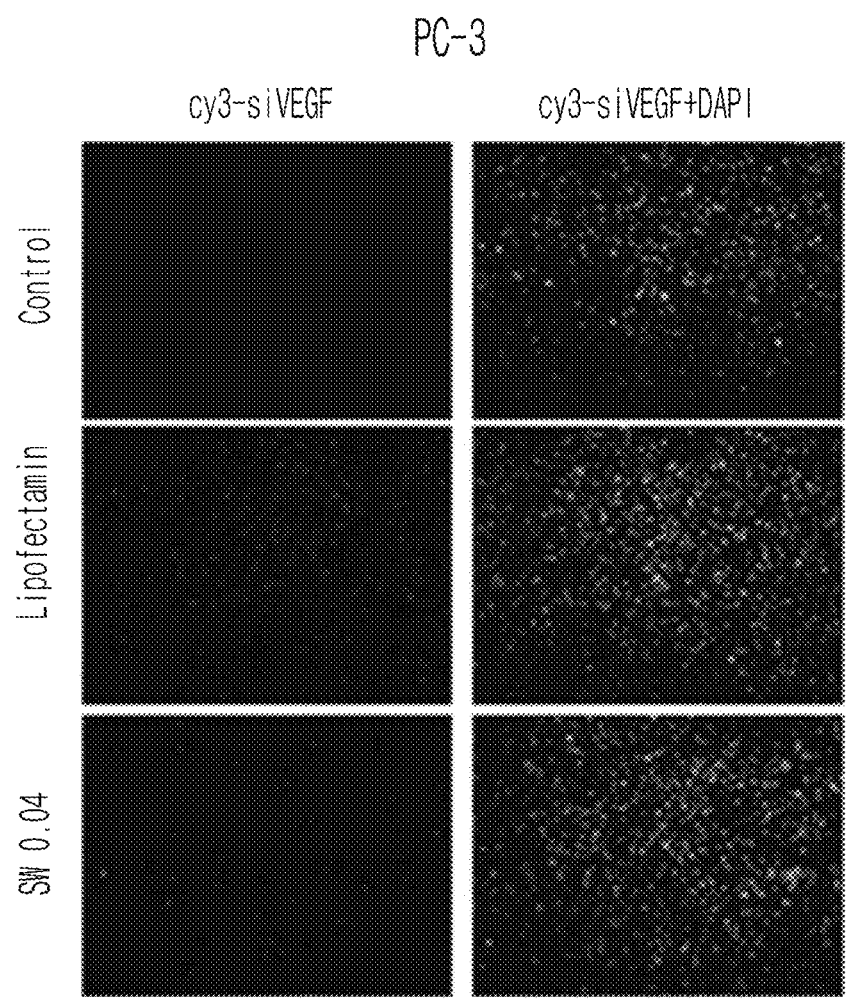
FIGS. 6A-6C are diagrams illustrating the transfection of PC-3 (FIG. 6A), iMAEC (FIG. 6B), and Cos-7 (FIG. 6C)
Figure 6B:
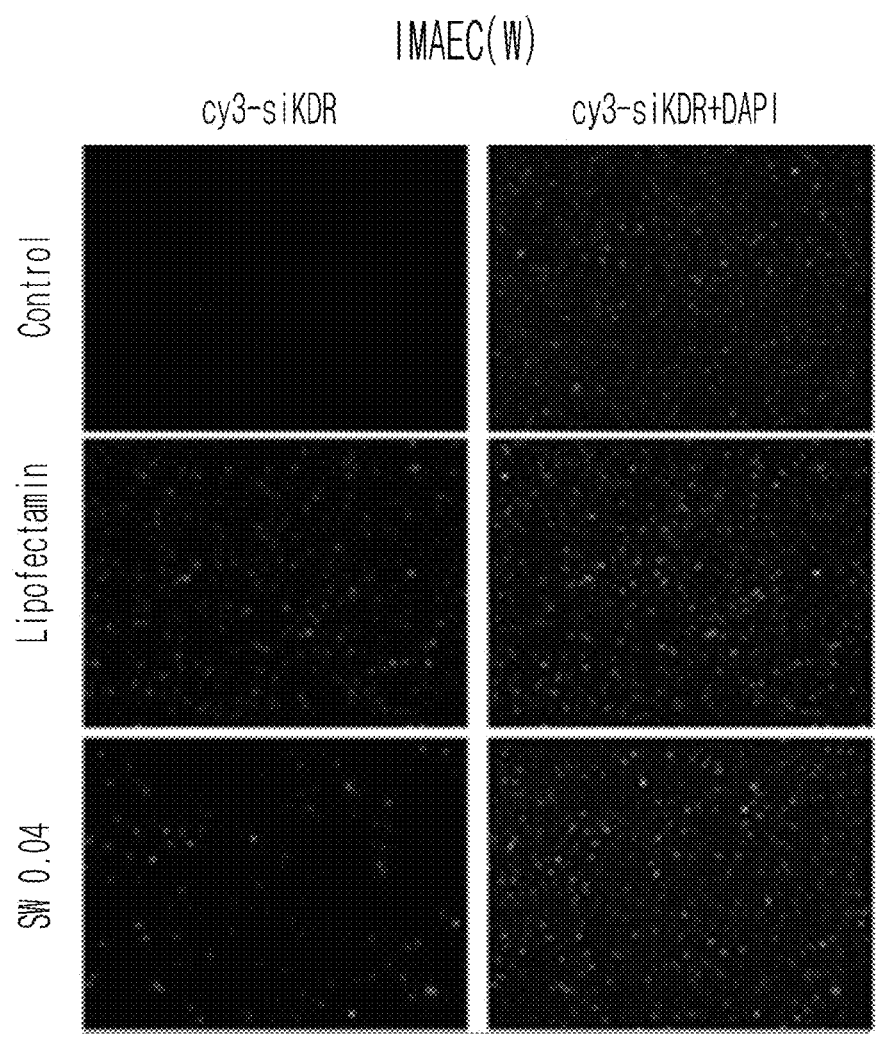
Figure 6C:
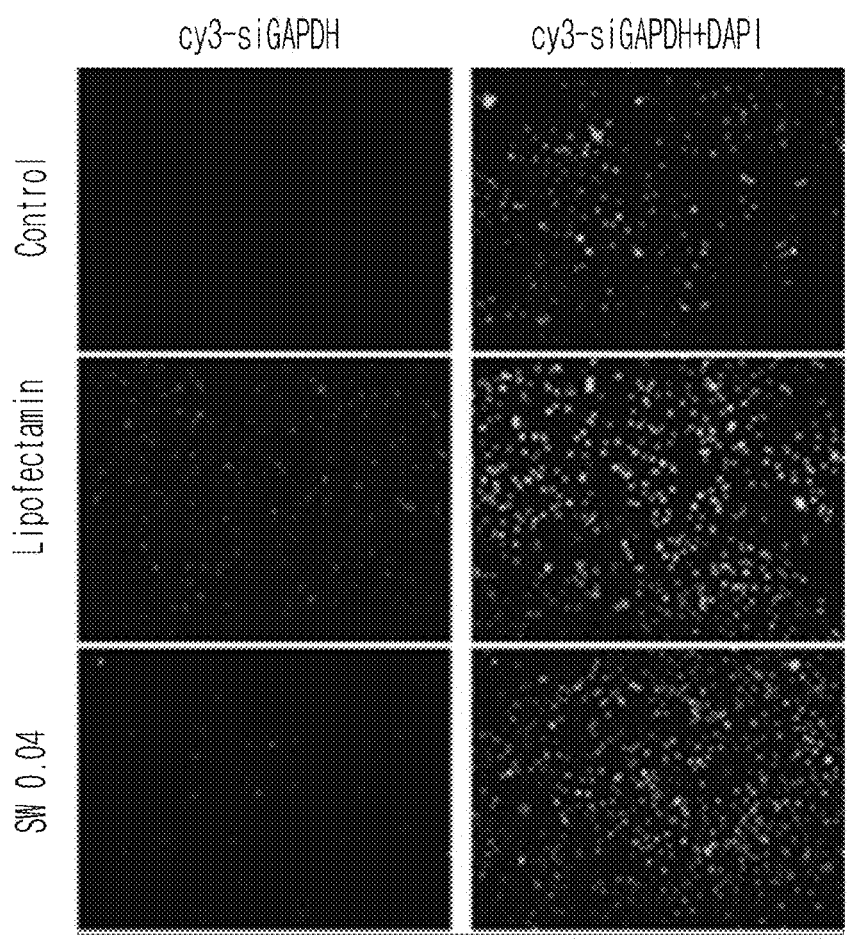

In addition, PC-3 (human prostate cancer cell line), iMAECs (immortalized mouse aortic endothelial cells), and COS-7, and COS-7 (monkey kidney fibroblast cells) were transfected with Cy3-labeled VEGF, KDR, and GAPDH siRNA using extracorporeal shockwave by the same manner as described in the above. As a result, as shown in FIG. 6, the target gene expression was suppressed (FIG. 6).

These results suggest that siRNA was delivered into cells by low-energy extracorporeal shockwave and inhibited the expression of target genes Experimental Example 3: Confirmation of Transfection Mechanism Induced by Extracorporeal Shockwave According to the previous reports, a temporary pore is made in the cell membrane when the transfection was induced by extracorporeal shockwave, and then a target gene was transfected through the generated pore.

To confirm whether the siRNA transfection by extracorporeal shockwave was due to the pore generated temporarily, Cy3-labeled VEGFR2 siRNA was added to the culture medium of HUVECs above, which was then treated with extracorporeal shockwave (0.04 mJ/mm$^2$), followed by culture for 48 hours. The transfection effect was examined by immunofluorescent staining performed at the time point of 0 min, 5 min, 24 hr, and 48 hr, respectively.

As a result, as shown in FIG. 7, HUVECs were not transfected with siRNA by the treatment of extracorporeal shockwave for the first 0~5 minutes (FIG. 7). However, HUVECs were successfully transfected with siRNA at the time during the culture, which was confirmed at the time points of 1, 3, 6, 24, and 48 hr (FIG. 7).

To confirm whether the pore formation in the cell membrane caused by extracorporeal shockwave was essential for the siRNA transfection, the culture time required for the transfection of HUVECs with siRNA was investigated. To do so, the extracorporeal shockwave treated medium was replaced. Particularly, HUVECs were transfected with Cy3-labeled VEGFR2 siRNA by using extracorporeal shockwave (0.04 mJ/mm$^2$), followed by culture for a designated period. Then, the medium was replaced with siRNA free-medium, followed by further culture for 24 hours.

As a result, as shown in FIG. 8A, the HUVECs treated with extracorporeal shockwave and cultured for 5 minutes were not transfected with Cy3-labeled VEGFR2 siRNA, while the HUVECs cultured for 24 hours were transfected with Cy3-labelled VEGFR2 siRNA with high efficiency (FIG. 8A).

In the previous study, it was proposed that the transfection efficiency of a gene by extracorporeal shockwave was achieved by the pores generated in the cell membrane several seconds after the shockwave treatment. However, the transfection with siRNA induced by extracorporeal shockwave required a certain period of culture time after the treatment of extracorporeal shockwave in this invention, which suggested that the gene transfection using extracorporeal shockwave was not attributed to the pores formed in the cell membrane.

To investigate whether the secretion of siRNA carriers induced by extracorporeal played an important role in the siRNA transfection, HUVECs were transfected with CY3-labeled VEFGR2 siRNAs under the effect of extracorporeal shockwave or without the effect of extracorporeal shockwave, followed by culture for 24 hours. 24 hours later, the extracorporeal shockwave-treated HUVECs culture medium was transferred to the HUVECs plate which had not been treated with extracorporeal shockwave, followed by further culture for 24 hours.

As a result, as shown in FIG. 8B, the cells non-treated with extracorporeal shockwave were transfected with VEFGR2 siRNA (FIG. 8B).

To confirm the siRNA migration by the secreted extracellular vesicles, the extracorporeal shockwave mediated transfection efficiency was measured by using MP-free medium. HUVECs were treated with Cy3-labeled VEFGR2 siRNAs and extracorporeal shockwave, followed by culture for 3 hours. Then, the medium was centrifuged at 170,000×g for 2 hours to eliminate extracellular vesicles. HUVECs were cultured in the extracellular vesicle free medium for 24 hours.

As a result, as shown in FIG. 8C, Cy3-labeled VEFGR2 siRNA was not detected in the HUVECs cultured in the extracellular vesicle free medium. However, it was confirmed that Cy3-labeled VEFGR2 siRNA was delivered successfully into the HUVECs cultured in the extracellular vesicle containing medium.

The above results suggest that the gene transfection factor of extracorporeal shockwave could be delivered through a carrier (for example, extracellular vesicle or protein). The present invention proved that extracorporeal shockwave could promote the secretion of extracellular vesicles and thus can be used for siRNA delivery.

Experimental Example 4: Confirmation of Transfection Effect Induced by Extracorporeal Shockwave Ex Vivo To investigate the siRNA transfection efficiency induced by extracorporeal shockwave in blood vessels, aorta ring assay was performed for ex vivo angiogenesis.

Particularly, mouse aortic ring angiogenesis assay was performed according to the conventional method informed to those in the art (Blache et al. *Angiogenesis* 4, 133.142 (2001), Masson, V. V. et al. *Biol Proced Online* 4, 24.31 (2002)). Briefly, the thoracic aorta of the mouse (C57BL/6J, 8 weeks old, male) was dissected, and the periaortic fibroadipose tissue was removed using microsurgery forceps and microdissection scissors under a stereo dissection microscope. The aortic ring (1 mm in length) was treated with 20 U/ml of heparin, which was fixed on Matrigel wherein the growth factor was deficient. The aortic ring was treated with VEGF/VEFGR2 siRNA together with VEGF (R&D system, Inc, Minneapolis, Minn., USA) or extracorporeal shockwave. Then, the aortic ring was cultured for 8 days at 37° C., 5% $CO_2$ condition which was the optimum condition for microvascular sprouting. The images were confirmed by using Olympus BX41 microscope (Olympus, Center Valley, Pa., USA).

As a result, as shown in FIGS. 9A and 9B, VEGF increased the number of microvasculature generated from the separated aortic ring, but when the aortic ring was transfected with VEFG siRNA by extracorporeal shockwave, the generation of microvasculature induced by VEGF was significantly suppressed (FIGS. 9A and 9B).

The above result indicates that siRNA was successfully introduced in cells in the course of transfection induced by extracorporeal shockwave and was ex vivo functioning smoothly as well. Therefore, the treatment of extracorporeal shockwave makes the direct introduction of siRNA into the cells of the extracted tissue and thus makes the siRNA be functioning well without any problem.

Experimental Example 5: Confirmation of CT-26 Tumor Treatment Effect of siRNA Transfection Induced by Extracorporeal Shockwave Ex Vivo The present inventors investigated that siRNA was transferred to tumor tissue by the treatment of extracorporeal shockwave and showed tumor suppression effect.

First, the experiment with the CT26 xenograft tumor mouse model was performed according to the Guidelines on Animal Experiment of Ewha Womans University Animal Care and Use Committee. Particularly, $4.0 \times 10^6$ CT26 cells were loaded in 0.3 ml of PBS (phosphate-buffered saline), which was subcutaneously injected into the lower side of an 8-week-old nude mouse (Central Lab Animal Inc., Seoul, Korea) using a 24-gauge needle. 2 weeks later, when the tumor was grown to reach the average volume of 1 $cm^3$, Cy3-labeled VEGFR2 siRNA was injected into the CT26 tumor nude mouse, followed by the treatment of extracorporeal shockwave (0.02 $mJ/mm^2$). Particularly, Cy3-labeled VEGFR2 siRNA diluted in 20 μl of sterilized PBS was directly injected into the tumor. The mouse group treated with Cy3-labeled VEGFR2 siRNA without the treatment of extracorporeal shockwave was used as the control. Relative fluorescence (red, Cy3-labeled siRNA; blue, nucleus) was visualized using a fluorescence microscope system (Olympus)

To analyze the density of microvasculature in the tumor, CD31 was immunostained by the conventional method known to those in the art, and CD31-positive microvasculature were counted (Takei et al. *Cancer research* 64, 3365.3370(2004), Takei et al. *Cancer* 107, 864.873(2006), Takei et al. *Cancer research* 61, 8486.8491(2001)).

As a result, as shown in FIG. 10A, 0.02 $mJ/mm^2$ of extracorporeal shockwave was confirmed to be the optimum condition for the successful transfection of siRNA into the CT26 tumor (FIG. 10A). Numbers of tumor cells were lost with 0.04 $mJ/mm^2$ of extracorporeal shockwave, suggesting that the tissues were severely damaged.

As shown in FIGS. 10B and 10C, the control tumor group displayed high VEFG expression. In the meantime, in the tumor group treated with extracorporeal shockwave (0.02 $mJ/mm^2$), only a small amount of VEFG was expressed (FIGS. 10B and 10C). The control tumor group displayed a strong CD31 staining (red), suggesting that the density of microvasculature was high. On the other hand, the group treated with extracorporeal shockwave exhibited weak CD31 staining, indicating a decrease of microvasculature (FIGS. 10D and 10E). The above results indicate that the direct insertion of siRNA in the cancer tissue had the treatment effect by reducing angiogenesis of microvasculature. Therefore, the method of the invention for the direct introduction of siRNA can be used as a treatment method.

Experimental Example 6: Analysis of Extracellular Vesicles Secreted by Extracorporeal Shockwave To investigate the mechanism of extracellular vesicle secretion from cells by extracorporeal shockwave, NTA (Nanoparticle Tracking Analysis) and FACS were performed by using NanoSight NS300 (Malvern Instruments, Malvern, UK), followed by observation under transmission microscope.

Particularly, FACS was performed by using BD FACS Canto II (Beckman Coulter, Brea, Calif., USA). Particles were grouped in 220, 440, 880, and 1,340 nm groups according to the standard-sized beads. To collect extracellular vesicle data, the beads were transferred through a flow cytometer with a default setting, from ich FSC (forward scattering) measurement average was calculated.

The in vitro extracorporeal shockwave experiment was performed by the same manner as described in Experimental Example 1. The fused HUVECs were cultured in a 35 mm culture dish, followed by the treatment of extracorporeal shockwave. The control was prepared by the same manner but not treated with extracorporeal shockwave. For FACS analysis, the collected samples were centrifuged at 180×g for 10 minutes to eliminate cell debris. The obtained supernatant was transferred into a new tube, followed by centrifugation at 1,500×g for 10 minutes to eliminate bigger particles. The supernatant was transferred into a 5 ml round-bottom tube for further FACS. The size and the number of extracellular vesicles were measured by using BD FACSCanto II (Beckman Coulter). The size of extracellular vesicles was measured by using SPHERO™ Flow Cytometry Nano Polystyrene and Nano Fluorescent Size Standard Kits (Spherotech, Lake Forest, Ill., USA). To reduce the error, extracellular vesicles were analyzed manually and automatically for 100 seconds Microvesicles were analyzed by using NanoSight NS300 (Malvern Instruments, Malvern, UK), by which the Brownian motion of nanoparticles in the liquid suspension could be traced by particle-by-particle basis. Nanoparticle tracking analysis (NTA) 3.0 software was used for the analysis of the size and concentration of microvesicles. The sample was prepared by the same manner as described for the preparation of FACS sample above and the sample was diluted at the ratio of 1:10.

To identify extracellular vesicles by using transmission electron microscope, cells were perfused in 0.1 M phosphate buffer containing 2% glutaraldehyde and 2% paraformaldehyde. The prepared cell blocks were post-fixed in 2% osmium tetroxide, followed by dehydration. Then, the cell blocks were fixed in epoxy resin. The target area of interest was selected from the 1 μm thick sections, followed by staining with toluidine blue. Then, thin sections were prepared (60×60 nm) by using an ultramicrotome (Reichert-Jung/Leica Microsystems, Wetzlar, Germany). The thin sections were stained with 1~2% uranyl acetate, and then stained with 1% lead citrate. The stained sections were observed under H-7650 transmission electron microscope (Hitachi, Tokyo, Japan) and photographed.

As a result of NTA, as shown in FIG. 11, the secretion of extracellular vesicles was increased for the first 30 minutes~1 hour after the treatment of extracorporeal shockwave but thereafter it slowly decreased (FIG. 11). According to the treatment of extracorporeal shockwave, comparatively large particles (>200 mm) were increased more than small particles (FIG. 11).

As a result of FACS, as shown in FIGS. 12A and 12B, consistently with the NTA results, the number of extracellular vesicles was significantly increased 30 minutes after the treatment of extracorporeal shockwave but decreased slowly thereafter (FIGS. 12A and 12B). The above results indicate that the secretion of extracellular vesicles was induced by extracorporeal shockwave very shortly after the treatment of extracorporeal shockwave. From the distribution analysis of large extracellular vesicles, it was confirmed that such extracellular vesicles in the diameter of 220 nm~440 nm were immediately increased by the treatment of extracorporeal shockwave. The results of NanoSight and FACS indicate that the treatment of extracorporeal shockwave induced the secretion of extracellular vesicles in the diameter of 200~500 nm significantly for the first 30 minutes and 1 hour after the treatment.

It was also confirmed under transmission electron microscope that the number of extracellular vesicles was increased along the multi-vesicular body and cell membrane of HUVECs in the culture medium (FIGS. 13A and 13B).

After the treatment of extracorporeal shockwave, the incorporation of siGlO was investigated by using NanoSight (Malvern Instruments).

As a result, as shown in FIGS. 14A and 14B, the absolute number of extracellular vesicles over 200 mm in diameter was smaller than that of extracellular vesicles below 200 nm, but the large extracellular vesicles absorbed siGlO more than 10 times than those extracellular vesicles in the size of 100 nm or less and in the size of 100~200 nm. (FIGS. 14A and 14B).

The results of Example 3 and Example 6 indicate that the extracellular vesicles secreted by the treatment of extracorporeal shockwave interact with siRNA and can be transfected into the extracorporeal shockwave non-treated cells.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

---

What is claimed is:

1. A method for promoting the secretion of extracellular vesicles from cells comprising the steps of:
treating cells or a subject with an extracorporeal shockwave, and obtaining the extracellular vesicles.

2. The method for promoting the secretion of extracellular vesicles according to claim 1, wherein the cells are separated from a subject.

3. The method for promoting the secretion of extracellular vesicles according to claim 1, wherein the extracorporeal shockwave is treated at the energy levels of 0.01~1.0 mJ/mm$^2$.

4. The method for promoting the secretion of extracellular vesicles according to claim 1, wherein the extracellular vesicles are selected from the group consisting of exosomes, ectosomes, microvesicles, and apoptotic bodies.

5. A method for producing extracellular vesicles including one or more materials selected from the group consisting of nucleic acids, proteins, and compounds, comprising the steps of:
treating cells with an extracorporeal shockwave, and obtaining the extracellular vesicles.

6. The method for producing extracellular vesicles according to claim 5, wherein the extracorporeal shockwave is treated at the energy levels of 0.01~1.0 mJ/mm$^2$.

7. The method for producing extracellular vesicles according to claim 5, wherein the extracellular vesicles are selected from the group consisting of exosomes, ectosomes, microvesicles, and apoptotic bodies.

8. The method for producing extracellular vesicles according to claim 5, wherein the nucleic acid is selected from the group consisting of DNA, RNA, microRNA, small interfering RNA(siRNA), small nucleolar RNA(snoRNA) and long non-coding RNA(lncRNA).

9. The method of claim 1, wherein the cells are endothelial cells.

10. The method of claim 1, wherein the cells are smooth muscle cells, colon adenocarcinoma cells, prostate cancer cells, mouse aortic endothelial cells or kidney fibroblasts.

11. The method of claim 5, wherein the cells are endothelial cells.

12. The method of claim 5, wherein the cells are smooth muscle cells, colon adenocarcinoma cells, prostate cancer cells, mouse aortic endothelial cells or kidney fibroblasts.

* * * * *